United States Patent
Uehata et al.

(10) Patent No.: US 8,940,247 B2
(45) Date of Patent: Jan. 27, 2015

(54) PORTABLE ANALYZER

(75) Inventors: Yoshiharu Uehata, Kyoto (JP);
Hiroyuki Nakanishi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 224 days.

(21) Appl. No.: 12/922,109

(22) PCT Filed: Mar. 17, 2009

(86) PCT No.: PCT/JP2009/055206
§ 371 (c)(1),
(2), (4) Date: Sep. 10, 2010

(87) PCT Pub. No.: WO2009/116544
PCT Pub. Date: Sep. 24, 2009

(65) Prior Publication Data
US 2011/0008880 A1 Jan. 13, 2011

(30) Foreign Application Priority Data

Mar. 18, 2008 (JP) .................... 2008-069187

(51) Int. Cl.
*G01N 31/22* (2006.01)
*G01N 35/00* (2006.01)
(Continued)

(52) U.S. Cl.
CPC ............ *G01N 35/00029* (2013.01); *G01N 2035/00108* (2013.01); *G01N 21/8483* (2013.01); *G01N 33/4875* (2013.01); *B01L 2300/0825* (2013.01); *B01L 2400/0481* (2013.01); *G01N 2035/00306* (2013.01)
USPC ................... 422/404; 422/430; 422/560

(58) Field of Classification Search
USPC ............................ 422/404, 400, 560
See application file for complete search history.

(56) References Cited

U.S. PATENT DOCUMENTS

| 4,833,088 A | 5/1989 | DeSimone et al. ........... 435/289 |
| 5,575,403 A * | 11/1996 | Charlton et al. .............. 221/31 |
| 2003/0031591 A1 | 2/2003 | Whitson et al. |

(Continued)

FOREIGN PATENT DOCUMENTS

| JP | 58-107333 A | 7/1983 |
| JP | H01-82814 U | 6/1989 |

(Continued)

OTHER PUBLICATIONS

International Search Report issued in PCT Application No. PCT/JP2009/055206.

(Continued)

*Primary Examiner* — Lyle Alexander
(74) *Attorney, Agent, or Firm* — Morgan, Lewis & Bockius LLP

(57) ABSTRACT

A portable analyzer A1 includes: hole forming means designed to form a hole 3 for insertion of a specimen sampling implement 6 therein; and analyzing means capable of analyzing a specimen when the sampling implement 6 is inserted into the hole 3, the hole forming means including a first member 1 having a first region R1 corresponding to a portion of an internal surface of the hole 3, and a second member 2 having a second region R2 corresponding to another portion of the internal surface of the hole 3. The first and second members 1 and 2 are capable of relative movement while being coupled to each other, the relative movement causing at least one of the first and second regions R1 and R2 to be exposed to outside for easy cleaning thereof.

12 Claims, 15 Drawing Sheets

(51) Int. Cl.
*G01N 21/84* (2006.01)
*G01N 33/487* (2006.01)

(56) References Cited

U.S. PATENT DOCUMENTS

| | | | |
|---|---|---|---|
| 2005/0124060 A1 | 6/2005 | Yamaguchi et al. | 435/287.9 |
| 2007/0263046 A1 | 11/2007 | Iwasa et al. | |
| 2008/0089812 A1* | 4/2008 | Uehata et al. | 422/104 |
| 2010/0014085 A1 | 1/2010 | Sekimoto | |

FOREIGN PATENT DOCUMENTS

| | | | | |
|---|---|---|---|---|
| JP | 01-119743 | | 11/1989 | G01N 21/78 |
| JP | 01-161419 A | | 11/1989 | |
| JP | 10-059460 A | | 3/1998 | |
| JP | 2002-267664 | | 9/2002 | G01N 33/52 |
| JP | 2002-267664 A | | 9/2002 | |
| JP | 2003-116628 A | | 4/2003 | |
| JP | 2003-139782 A | | 5/2003 | |
| JP | 2004-151082 | | 5/2004 | G01N 33/493 |
| JP | 2004-184255 | | 7/2004 | G01N 27/28 |
| JP | 2005-040267 A | | 2/2005 | |
| JP | 2005-143500 | | 6/2005 | C12M 1/34 |
| JP | 2005-143500 A | | 6/2005 | |
| JP | 2007-303968 | | 11/2007 | G01N 21/59 |
| WO | 2007/132903 A1 | | 11/2007 | |

OTHER PUBLICATIONS

Notification of Reasons for Rejection issued by the Japanese Patent Office in corresponding Japanese Patent Application No. 2010-503888 dated Apr. 23, 2013.

Extended European Search Report issued in related European Patent Application No. 09721545.3 dated Jun. 10, 2014.

* cited by examiner

PORTABLE ANALYZER

This application is a 371 filing based on PCT/JP2009/055206, filed Mar. 17, 2009, which claims priority to Japanese Application No. 2008-069187, filed Mar. 18, 2008, each of which is hereby incorporated by reference in its entirety.

TECHNICAL FIELD

The present invention relates to a portable analyzer which is suited for being carried and is used to analyze a desired specimen such as blood or urine.

BACKGROUND ART

Patent Documents 1 and 2 disclose specific examples of portable analyzers. The portable analyzers described in these Documents are of the type which includes a relatively rigid case incorporating therein devices and processing circuits for analyzing a predetermined specimen such as blood and which, as a whole, has a shape and size suited for being carried. The case has a front end portion formed with a hole and analysis of the specimen is possible when a specimen sampling implement is inserted into the hole.

With such an arrangement, a portable analyzer can be easily carried and is capable of performing a specimen analyzing operation repeatedly by replacement of the sampling implement. For example, a diabetic patient is desired to control his or her blood glucose level by measuring the blood glucose level within a predetermined time period after each meal. The above-described portable analyzer is suitable for such a use.

However, the above-described conventional technique still leaves room for improvements as described below.

That is, the sampling implement is inserted into the hole every time the analyzing operation is performed. For this reason, it is possible that the interior of the hole is stained if the sample implement is stained. A specimen, such as blood, is likely to adhere to the outer surface, in particular, of the sampling implement and in some cases the specimen thus adhering intrudes into the hole. In the case where the user does not sufficiently understand how to use the portable analyzer, the user might stain the interior of the hole by introducing the specimen directly into the hole without using the sampling implement. For the portable analyzer, the stained condition of the interior of the hole as described above is, in itself, not preferable from the viewpoint of hygiene. In the case where the portable analyzer is designed to analyze the specimen by an optical technique for example, the interior of the hole is often provided with a transparent aperture for applying the specimen with light from a light source and guiding reflected light or transmitted light from the specimen toward a light-receiving device. Therefore, it is difficult for the specimen to be correctly analyzed when the transmittance of the transparent aperture is impaired by stain on the transparent aperture. In the case where the portable analyzer is designed to analyze the specimen by an electrical or electrochemical technique unlike the former case, an electrode is sometimes placed within the hole. When such an electrode is stained, the specimen is still difficult to analyze correctly.

The above-described conventional technique has not provided means for easily and properly cleaning the interior of the hole stained. In order to clean the interior of the hole, it has conventionally been necessary to disassemble the portable analyzer and expose a portion corresponding to the internal surface of the hole. However, such an operation is not easy. Further, after the portable analyzer has been disassembled, it is possible that some disassembled parts are lost.

Patent Document 1: Japanese Patent Laid-Open Publication No. 2007-303968

Patent Document 2: Japanese Patent Laid-Open Publication No. 2004-184255

DISCLOSURE OF THE INVENTION

Problems to be Solved by the Invention

An object of the present invention is to provide a portable analyzer which allows easy and proper cleaning of the interior of a hole for insertion of a specimen sampling implement therein when the interior of the hole is stained.

Means for Solving the Problems

In order to solve the foregoing problems, the present invention provides the following technical means.

According to the present invention, there is provided a portable analyzer comprising: hole forming means designed to form a hole for insertion of a specimen sampling implement therein; and analyzing means capable of analyzing a specimen when the sampling implement is inserted into the hole, the hole forming means including a first member having a first region corresponding to a portion of an internal surface of the hole, and a second member having a second region corresponding to another portion of the internal surface of the hole, wherein the first and second members are capable of relative movement while being coupled to each other, the relative movement enabling selective switching to one of a first state in which the first and second regions are positioned close to each other in opposed relation to form the hole and a second state in which at least one of the first and second regions is exposed to outside after the first and second regions have been released from the first state.

Preferably, the portable analyzer has an arrangement wherein: the first and second members are capable of rotating relative to each other in opposed directions in which the first and second members are opposed to each other in such a manner as to enable selective switching to be made between a state in which a first end portion of the first member and a first end portion of the second member are positioned close to each other in opposed relation and a state in which the first end portions of the first and second members are spaced apart from each other to define a flared open space therebetween; and the first state is established by positioning the first end portions close to each other in the opposed relation, while the second state established by spacing the first end portions apart from each other, the first and second regions fronting on the space between the first end portions when in the second state.

Preferably, the portable analyzer according to the present invention further comprises slide guide means capable of sliding the first and second members assuming the first state relative to each other in fixed directions intersecting the opposed directions, wherein the first and second members set in the first state are allowed to rotate relative to each other for switching to the second state only after the first and second members have been slid relative to each other by a predetermined amount of displacement in the fixed directions.

Preferably, the portable analyzer has an arrangement wherein: the slide guide means includes a guide slot provided at one of the first and second members and having a small width portion extending in the fixed directions and a large width portion extending continuously with one end of the small width portion, and a projecting portion provided at the other for engagement in the guide slot and having a noncircular sectional shape; when the projecting portion is engaged in the small width portion, the first and second members are allowed to slide relative to each other in the fixed directions with their relative rotation being inhibited; and when the projecting portion is engaged in the large width portion as a result of the relative sliding of the first and second members, the first and second members are allowed to rotate relative to each other.

Preferably, the portable analyzer according to the present invention further comprises auxiliary guide means designed to guide the second member in the opposed directions so as to bring the second member closer to the first member in returning the first and second members from the state in which the displacement takes place to the first state and then keep relative positional relation between the first and second members after the first and second members have been returned to the first state.

Preferably, the auxiliary guide means has an engagement projection provided at one of the first and second members and a guide surface provided at the other, the projection being designed to engage the guide surface so as to inhibit the first and second members in the first state from separating away from each other in the opposed directions.

Preferably, the guide surface is inclined at least partially to provide a play between the first and second members in the opposed directions when the second member moves forwardly of the first member from the first state.

Preferably, the portable analyzer has an arrangement wherein: the first and second members are capable of relative rotation about a central axis extending in opposed directions in which the first and second members are opposed to each other, the relative rotation enabling selective switching to one of the first and second states; and when in the second state, the first region is exposed to outside by failure to be positioned to face the second member, while the second region is exposed to outside by failure to be positioned to face the first member.

Preferably, the first and second members are capable of relative sliding in directions intersecting opposed directions in which the first and second members are opposed to each other, the relative sliding enabling selective switching to one of the first and second states.

Preferably, the portable analyzer according to the present invention further comprises a case which accommodates the analyzing means therein while covering a periphery of the first and second members in the first state, the case being divided into plural portions which cover the first and second members individually and which move relative to each other as the first and second members move relative to each other.

Preferably, the portable analyzer according to the present invention further comprises determination means which is capable of detecting a relative positional relation between the first and second members and determining whether or not the first and second members are correctly set in the first state, wherein in response to a determination by the determination means that the first and second members are not correctly set in the first state, an alarm operation is performed to provide a notification to that effect.

Preferably, the portable analyzer according to the present invention further comprises a locking mechanism which inhibits relative movement of the first and second members to keep the first and second members in the first state when the first and second members are set in the first state while allowing the relative movement of the first and second members in response to a predetermined operation.

Preferably, the portable analyzer has an arrangement wherein: the analyzing means is configured to carry out measurement on a predetermined element in the specimen by applying light to the specimen under a predetermined condition and receiving transmitted light or reflected light from the specimen; at least one of the first and second members is provided with a light transmissive member which allows light to pass therethrough; and the light transmissive member becomes exposed to outside to allow cleaning thereof when the first and second members are set in the second state.

Preferably, the portable analyzer has an arrangement wherein: the analyzing means is capable of detecting whether or not stain is present on the light transmissive member based on the amount of transmitted light through the light transmissive member; and in response to detection of stain on the light transmissive member, an alarm operation is performed to provide a notification to that effect.

Preferably, the portable analyzer has an arrangement wherein: the analyzing means is provided with an electrode placed in at least one of the first and second regions so as to come into contact with a predetermined portion of the sampling implement and is capable of carrying out measurement on a predetermined element of the specimen based on information obtained by utilizing the electrode; and the electrode becomes exposed to outside to allow cleaning thereof when the first and second members are set in the second state.

Preferably, the analyzing means is configured to measure a blood glucose level when the specimen is blood.

Other features and advantages of the present invention will become more apparent from the description of embodiments of the invention given below with reference to the accompanying drawings.

BEST MODE FOR CARRYING OUT THE INVENTION

Hereinafter, preferred embodiments of the present invention will be described specifically with reference to the drawings.

Figure 1:
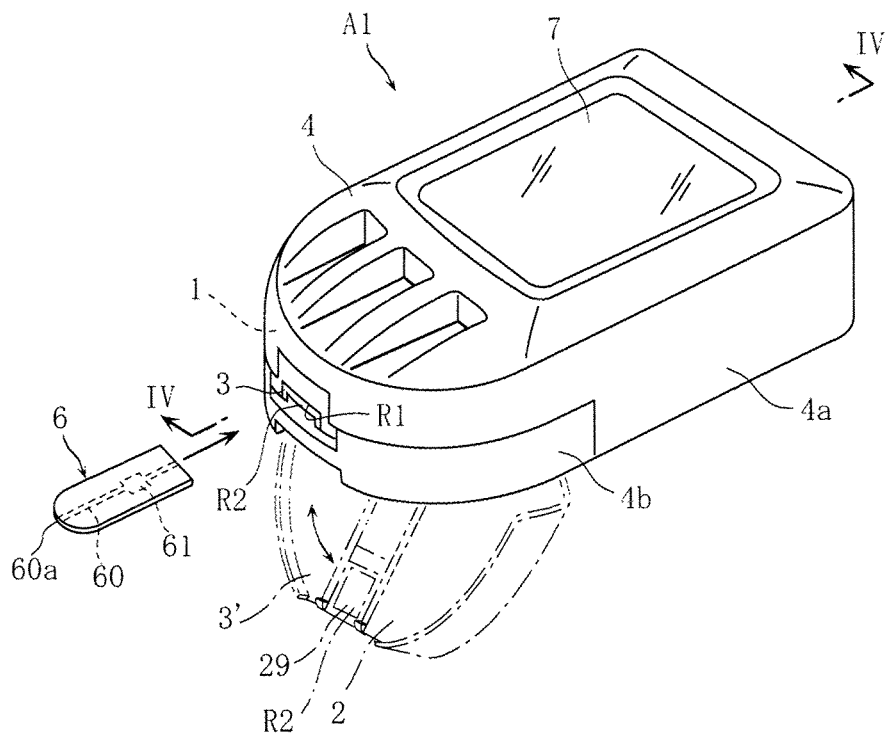
FIG. 1 is a perspective view illustrating an exemplary portable analyzer according to the present invention.
Figure 2:
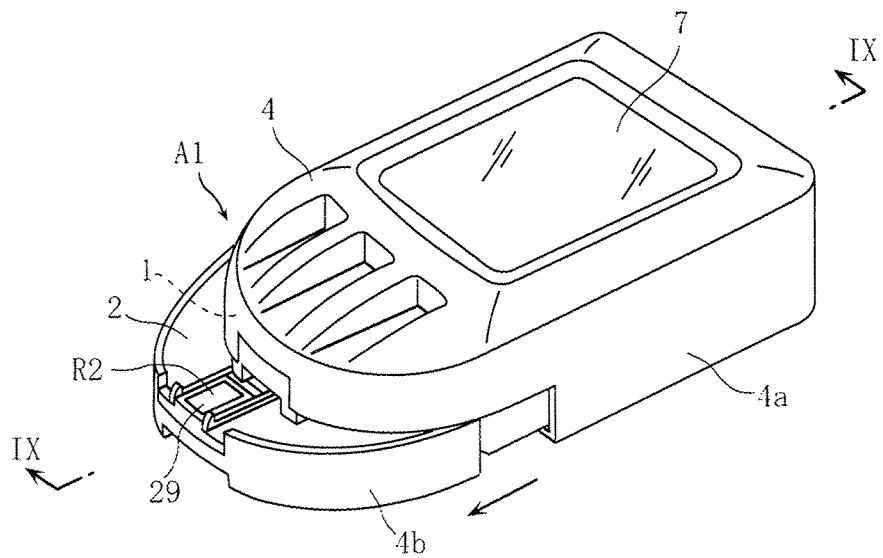
FIG. 2 is a perspective view illustrating a state in which predetermined portions of the portable analyzer illustrated in FIG. 1 are displaced relative to each other.
Figure 3:
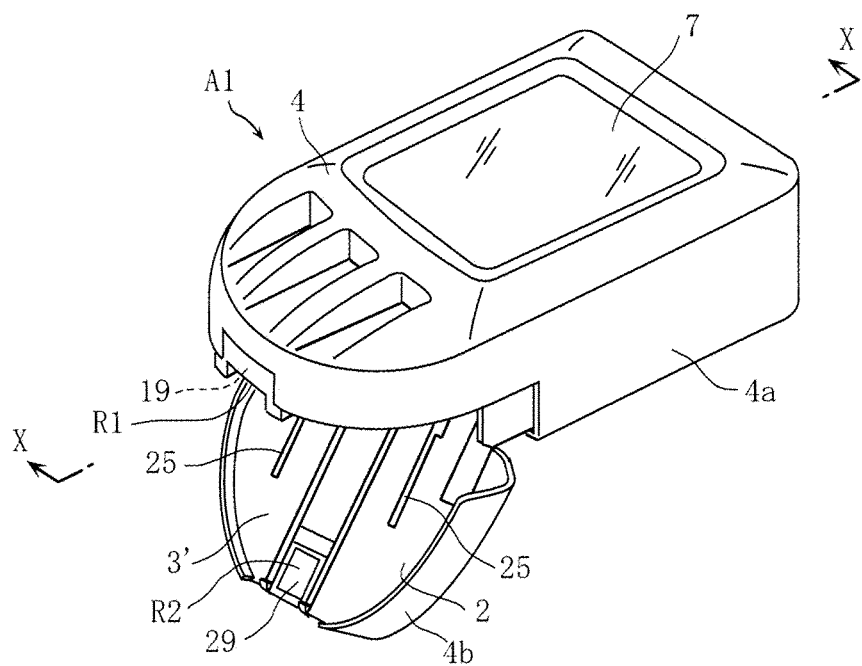
FIG. 3 is a perspective view illustrating a state in which the predetermined portions of the portable analyzer illustrated in FIG. 1 are open.

FIGS. 1 to 10 illustrate an exemplary portable analyzer according to the present invention. A portable analyzer A1 according to the present embodiment is capable of switching from a first state in which a hole 3 is formed as shown in FIG. 1 to a state in which a front portion is displaced as shown in FIG. 2 and then to a second state in which the front portion is open as shown in FIG. 3. The portable analyzer A1 is set in the first state shown in FIG. 1 when in storage and when analyzing a specimen. When the interior of the hole 3 is to be cleaned because of stain, the analyzer A1 is switched to the second state shown in FIG. 3 via the displaced state shown in FIG. 2.

The portable analyzer A1 has a shape and size suitable for being gripped by one hand of a user (for example, the analyzer A1 in the first state shown in FIG. 1 has an entire front-back dimension of about 6 to about 10 cm, a transverse width of about 4 to about 7 cm, and a thickness of about 1.5 to about 3.5 cm) and is designed as a blood glucose level measuring device. The portable analyzer A1 comprises first and second members 1 and 2 for forming the hole 3, a data processing section 5 and a display device 7 using a liquid crystal display panel, which are incorporated in a case 4 of relatively rigid synthetic resin. Though not shown, the case 4 also incorporates therein an electrical power source section provided with a battery or rechargeable battery for driving the data processing section 5 and the display device 7. The first and second members 1 and 2 are equivalent to an example of the "hole forming means" defined by the present invention.

The portable analyzer A1 is capable of measuring a glucose level in blood sampled using a sampling implement 6 by an optical technique. An existing method of measurement may be adopted as a method for the measurement. Specifically, the sampling implement 6 is of a disposable type which is shaped into a small piece formed therein with a capillary 60 which has an opening portion 60a at a tip of the sampling implement 6 and an intermediate portion forming a reaction portion 61 provided with a predetermined reagent, as shown in FIG. 1. When blood is dropped into the opening portion 60a, the blood proceeds within the capillary 50 by the capillary action and reaches the reaction portion 61 where the blood reacts with the reagent. In the reaction portion 61 a color corresponding to a blood glucose level is developed.

Figure 5:
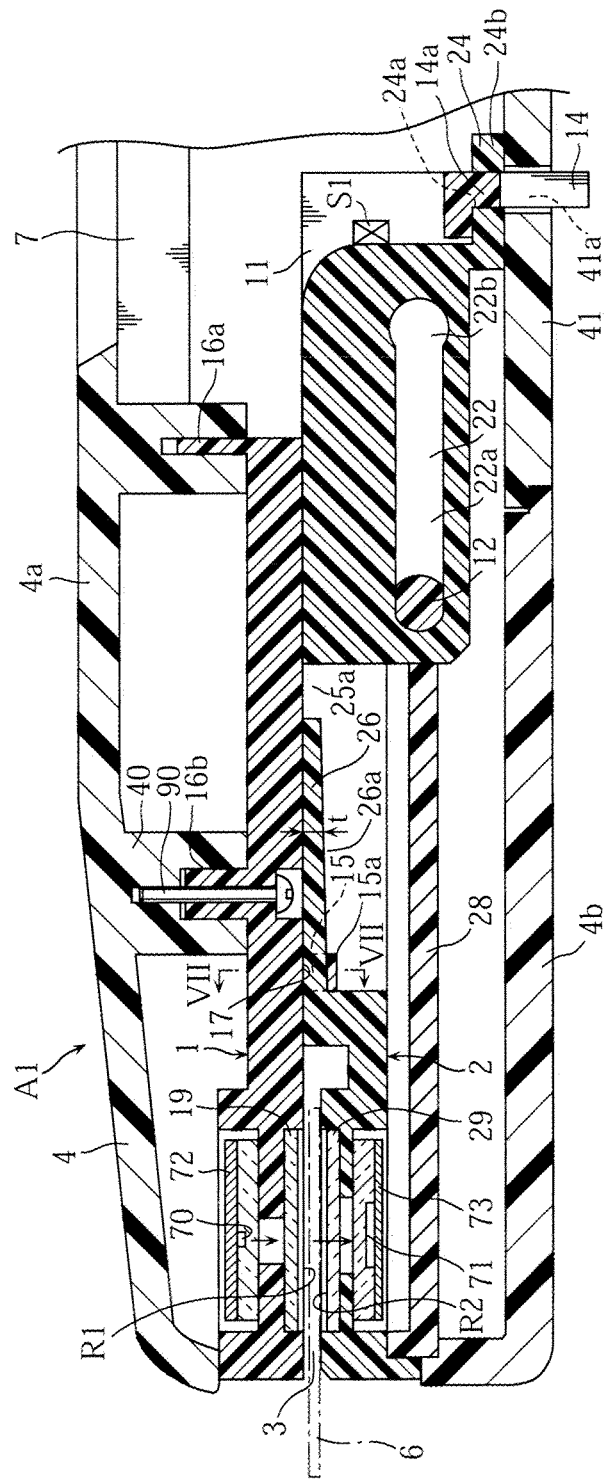
FIG. 5 is an enlarged sectional view of a relevant portion of FIG. 4.

As better shown in FIG. 5, the first and second members 1 and 2 are provided with a light source 70, such as an LED, and a light-receiving device 71 using a photodiode or the like. A configuration comprising the data processing section 5 in combination with the light source 70 and the light-receiving device 71 is an exemplary equivalent of the "analyzing means" defined by the present invention. The portable analyzer A1 employs a light transmission type analyzing system in which the light source 70 applies light to the reaction portion 61 with the sampling implement 6 being inserted into the hole 3 while the light-receiving device 71 receives transmitted light having passed through the reaction portion 61. The data processing section 5, which comprises a microcomputer, calculates a blood glucose level based on a signal outputted from the light-receiving device 71 and causes the display device 7 to show the resulting value. Though not shown, substrates 72 and 73 mounted with the light source 70 and the light-receiving device 71 both encapsulated with resin are wired to the data processing section 5.

The hole 3 is formed between the first and second members 1 and 2 vertically superposed on each other by being positioned close to (or into contact with) each other in opposed relation. The first member 1 has a first region R1 corresponding to a portion of the internal surface of the hole 3. The second member 2 has a second region R2 corresponding to another portion of the internal surface of the hole 3. The first and second members 1 and 2 are both formed of black-colored resin having a low reflectance from the viewpoint of reduction in the likelihood of scattering and reflection of light within the hole 3. The first and second regions R1 and R2 are provided with light transmissive members 19 and 29, respectively. These light transmissive members 19 and 29 serve to allow light to proceed from the light source 70 toward the light-receiving device 71 while inhibiting dust and the like from undesirably proceeding from the hole 3 toward the light source 70 and the light-receiving device 71. When the light transmissive members 19 and 29 are stained, cleaning of the light transmissive members 19 and 29 is required because accurate glucose level measurement becomes difficult.

The data processing section 5 is configured to be capable of determining whether or not the light transmissive members 19 and 29 are stained. More specifically, the case 4 is provided therein with a sensor (not shown) for determining whether or not the sampling implement 6 is inserted in the hole 3. When the sampling implement 6 is not inserted in the hole 3, the data processing section 5 causes the light source 70 to emit light, detects the amount of light received by the light-receiving device 71 and determines that the light transmissive members 19 and 29 are stained if the amount of light received is less than a predetermined value. Such a determination is made either repeatedly at predetermined time intervals for example or every time the sampling implement 6 is withdrawn from the hole 3 after completion of the glucose level measurement. If the light transmissive members 19 and 29 are determined as being stained, the display device 7 is caused to display a notification to that effect.

Figure 4:
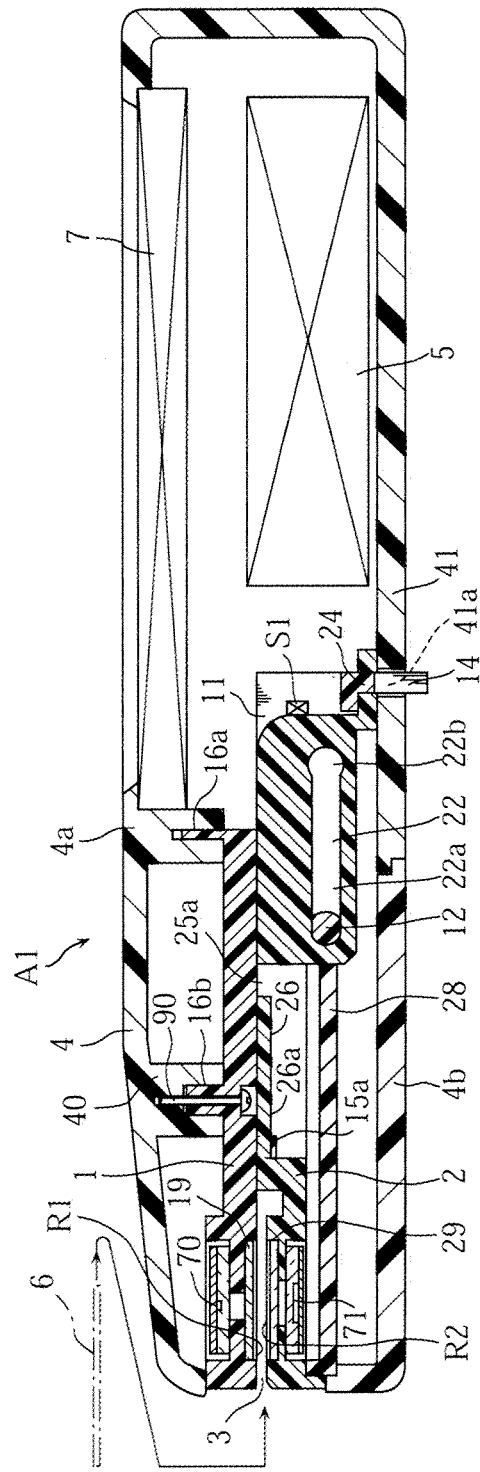
FIG. 4 is a sectional view taken on line IV-IV of FIG. 1.
Figure 6:
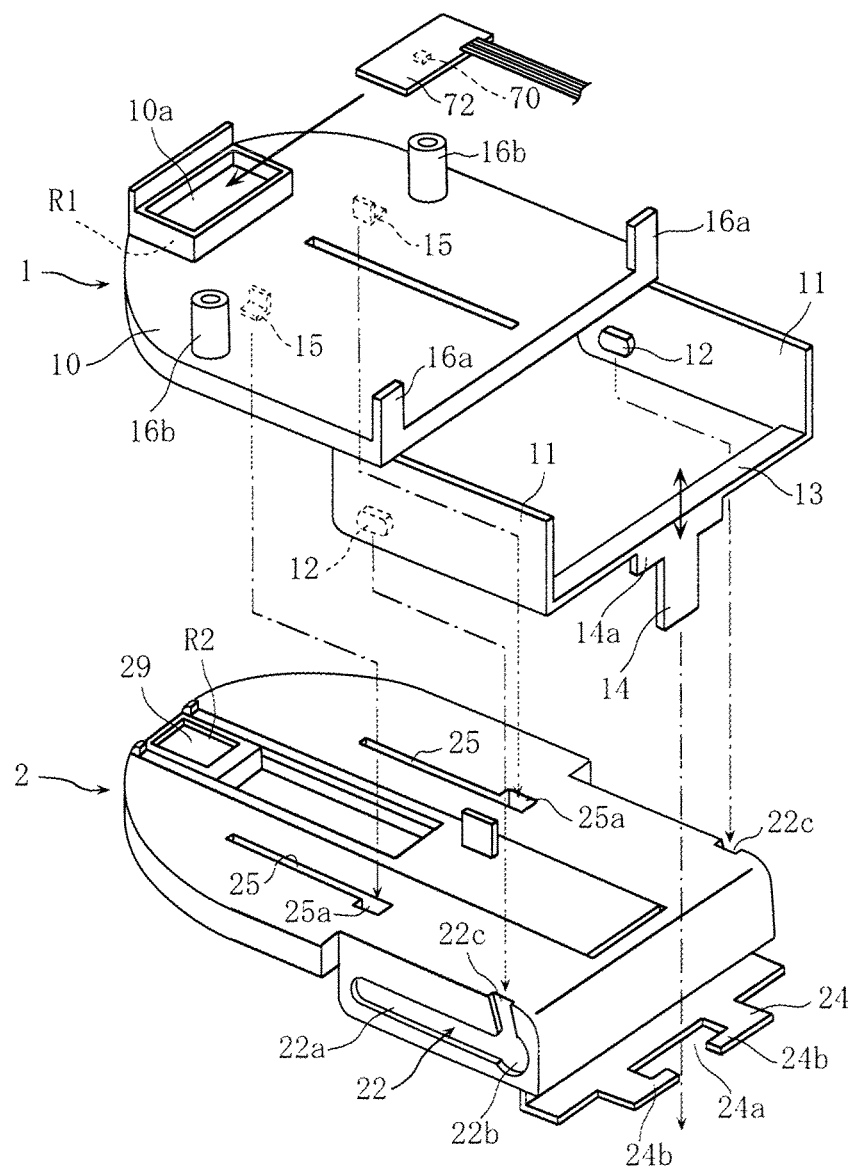
FIG. 6 is an exploded perspective view of first and second members of the portable analyzer illustrated in FIG. 1.

As better shown in FIG. 6, the first member 1 has an upper plate 10 having a front portion formed with a recess 10a to be fitted with a substrate 72 mounted with the light source 70 and a rear portion from which a pair of sidewalls 11 protrude downwardly. The inwardly oriented surfaces of the pair of sidewalls 11 are formed with a pair of projecting portions 12. The pair of sidewalls 11 are coupled to each other by way of a coupling portion 13 which is formed with a downwardly extending projection 14. The upper plate 10 has a top surface formed with one or more projections 16a and bosses 16b. As shown in FIGS. 4 and 5, the first member 1 is fixedly mounted on an upper wall 40 of the case 4 by bringing its projections 16a and bosses 16b into engagement with appropriate recesses formed in a lower surface of the upper wall 40 of the case 4 by means of screws 90.

The second member 2 is slidable relative to the first member 1 in the front-back direction (in the direction in which the sampling implement 6 is inserted into or withdrawn from the hole 3). The second member 2 is vertically rotatable relative to the first member 1.

More specifically, the second member 2 is in the form shown in FIG. 6 and has opposite side surfaces adjacent the rear side thereof which are formed with guide slots 22 allowing the projecting portions 12 of the first member 1 to be engaged therein. The structure comprising the projecting portions 12 and the guide slots 22 in combination is an exemplary equivalent of the "slide guide means" defined by the present invention. The guide slots 22 each have a shape comprising a small width portion 22a extending in the front-back direction and a large width portion 22b having a larger vertical width than the small width portion 22a and extending continuously with the rear end of the small width portion 22a. The large width portion 22b has an upper portion formed with a notch-like slot 22c for allowing the associated projecting portion 12 to enter the guide slot 22 smoothly. (Note that the slot 22c is not shown in figures other than FIG. 6.) By engaging the projecting portions 12 into the associated guide slots 22, the second member 2 can be slid while being supported by the first member 1 and, hence, the first and second members 1 and 2 can be set in the displaced state shown in FIGS. 2 and 9.

Figure 9:
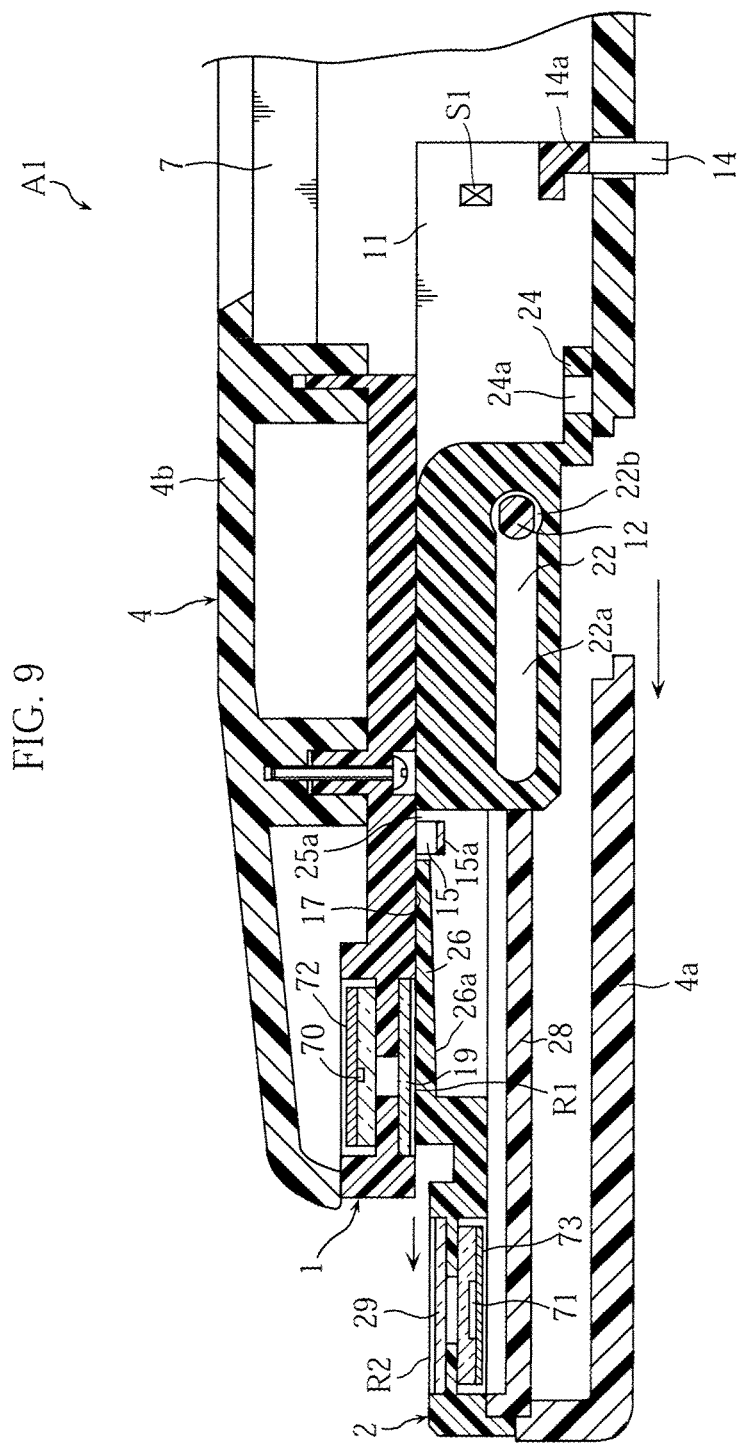
FIG. 9 is a sectional view, taken on line IX-IX of FIG. 2, of a relevant portion.

The projecting portions 12, each of which has a noncircular sectional shape, inhibit the second member 2 from rotating relative to the first member 1 when engaged in the small width portions 22a of the guide slots 22. When the second member 2 is moved forward by a predetermined distance as shown in FIG. 9, the projecting portions 12 become engaged in the large width portions 22b, thus allowing the second member 2 to rotate relative to the first member 1. Therefore, the first and second members 1 and 2 can be set in the second state shown in FIGS. 3 and 10. In the second state, the front end portions of the first and second members 1 and 2 are largely spaced apart from each other to define a flared space 3' therebetween.

Figure 7:
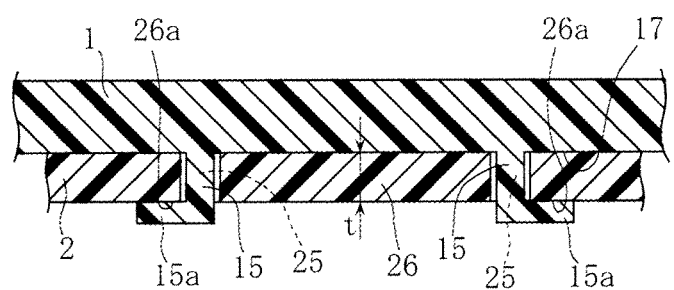
FIG. 7 is a sectional view taken on line VII-VII of FIG. 5.
Figure 8:
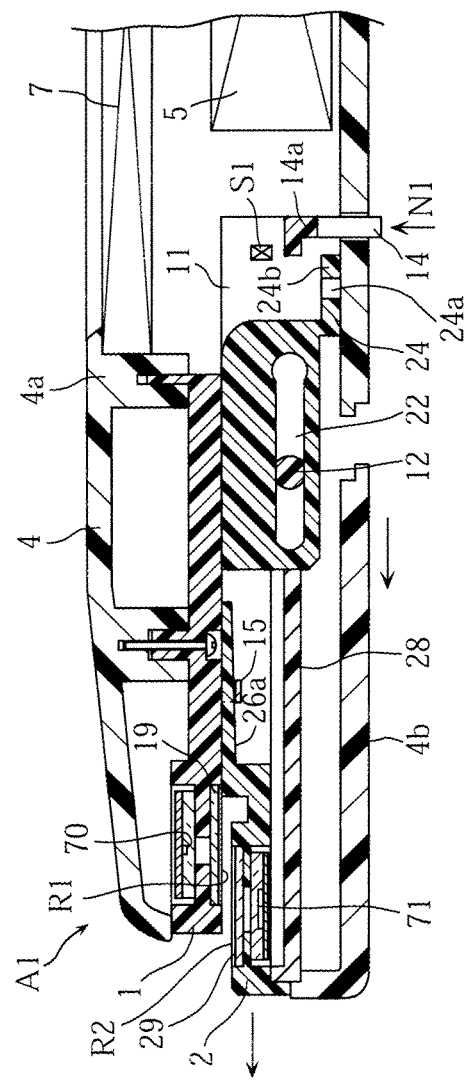
FIG. 8 is a sectional view of a relevant portion for illustrating a state in which the second member of the portable analyzer illustrated in FIG. 1 starts moving forward.

As better shown in FIG. 6, the second member 2 has an upper side formed with a pair of slits 25 each extending in the front-back direction and each having a large width portion forming a rear portion thereof. On the other hand, the upper plate 10 of the first member 1 has a lower surface formed with a pair of engagement projections 15 which become fitted into the pair of slits 25 from the large width portions 25a. Each of the projections 15 is L-shaped in section as shown in FIG. 7 with a horizontal portion 15a forming a lower end portion thereof. The second member 2 has a sandwiched portion 26 sandwiched between the horizontal portions 15a and a downwardly oriented surface 17 of the first member 1, the sandwiched portion 26 having a lower surface serving as a guide surface 26a. The structure comprising the guide surface 26a and the projections 15 in combination is an exemplary equivalent of the "auxiliary guide means" defined by the present invention.

As shown in FIG. 5, the sandwiched portion 26 has a wall thickness t which increases as it extends forward and, therefore, the guide surface 26a is inclined downwardly in the forward direction. When the first and second members 1 and 2 are set in the first state shown in FIG. 5, the sandwiched portion 26 is sandwiched between the horizontal portions 15a of the projections 15 and the downwardly oriented surface 17 of the first member 1 without clearance, so that the first and second members 1 and 2 are fixedly positioned relative to each other in the vertical direction.

The first member 1 is provided with a sensor S1 for detecting the position of the second member 2. Though the sensor S1 detects the rear end of the second member 2 according to the present embodiment, the position to be detected is not limited thereto. The data processing section 5 is configured to determine whether or not the first and second members 1 and 2 have a proper original positional relation with each other in the first state based on an output signal from the sensor S1. When the first and second members 1 and 2 do not have the proper positional relation with each other, the display device 7 is caused to display a notification to that effect.

As better shown in FIG. 6, the second member 2 has a rear portion provided with a engagement frame 24 defining a cutout hole 24a having an open rear portion for the projection 14 of the first member 1 to be inserted therethrough. The structure comprising the combination of these components is an exemplary equivalent of the "locking mechanism" defined by the present invention. In the first state, a large width portion 14a forming an upper portion of the projection 14 is positioned within the cutout hole 24a, while a pair of stopper portions 24b forming a rear portion of the frame 24 engage the rear surface of the large width portion 14a. This prevents the second member 2 from moving forwardly of the first member 1. As shown in FIGS. 4 and 5, the lower end portion of the projection 14 is inserted through a hole 41a extending through a lower wall 41 of the case 4 and protrudes downwardly from the case 4. When the user presses the lower end portion of the projection 14 upwardly as indicated by arrow N1 in FIG. 8 to raise the large width portion 14a to above the stopper portions 24b, the engagement between these components is released to allow the second member 2 to move forward. When the projection 14 is pressed upwardly, the coupling portion 13 shown in FIG. 6 bends upwardly. However, when the projection 14 is released from the pressed state, the projection 14 descends to its original position by the elastic restoring force of the coupling portion 13.

The case 4 is divided into an auxiliary portion 4b covering the lower surface and side surfaces of the second member 2 and a main portion 4a covering other portions. The auxiliary portion 4b and the second member 2 are assembled together via an auxiliary cover 28 by means of a screw shown) for example. As the second member 2 moves forward and rotates, the auxiliary portion 4b moves forward and rotates away from the main portion 4a. The auxiliary portion 4b and the main portion 4a are designed to come into appropriate contact with each other in the first state so as not to form a large gap therebetween.

Description will be made of the operation of the portable analyzer A1.

Normally, the portable analyzer A1 is set in the first state in which the first and second members 1 and 2 are positioned close to each other in opposed relation to form the hole 3 defined between the first and second regions R1 and R2. In blood glucose level measurement, the sampling implement 6 is inserted into the hole 3 of the analyzer A1 assuming the first state. Subsequently, blood is dropped into the opening portion 60a of the sampling implement 6 and then allowed to proceed up to the reaction portion 61. In the blood glucose level measurement, the light source 70 applies light to the reaction portion 61 of the sampling implement 6, while the light-receiving device 71 receives transmitted light having passed through the reaction portion 61, as already described. The data processing section 5 determines the transmittance of the reaction portion 61, calculates the glucose level in the blood based on the transmittance, and causes the display device 7 to show the value thus obtained. After completion of the blood glucose level measurement, the user withdraws the sampling implement 6 from the hole 3 and disposes of it.

In the aforementioned first state, the projection 14 and the frame 24 engage each other to lock the first and second members 1 and 2 in order to prevent the first and second members 1 and 2 from sliding relative to each other in the front-back direction. Therefore, the positional relation between, for example, the light source 70 and the light-receiving device 71 in the front-back direction can be prevented from becoming improper. In addition, as described with reference to FIG. 7, the first and second members 1 and 2 can be prevented from being vertically displaced relative to each other because the sandwiched portion 26 of the second member 2 is sandwiched between the horizontal portions 15a of the projections 15 and the downwardly oriented surface 17 of the first member 1 without clearance. Therefore, the vertical spacing between the light source 70 and the light-receiving device 71 can be maintained properly, which makes it possible to ensure accurate blood glucose level measurement.

When the surface of the sampling implement 6 to be inserted into the hole 3 is stained, it is possible that the light transmissive members 19 and 29 become stained also. In the case where the user does not sufficiently understand how to use the portable analyzer A1, the user might drop blood directly into the front open end of the hole 3 without inserting the sampling implement 6 into the hole 3. In such a case also, the light transmissive members 19 and 29 become stained. As already described, the data processing section 5 has the function of determining whether or not the light transmissive members 19 and 20 are stained and, when the light transmissive members 19 and 20 are determined as being stained, the data processing section 5 causes the display device 7 to provide a notification to that effect. Therefore, when the light transmissive members 19 and 29 are stained, the user can recognize that fact appropriately and can clean the light transmissive members 19 and 29 with good timing.

Figure 10:
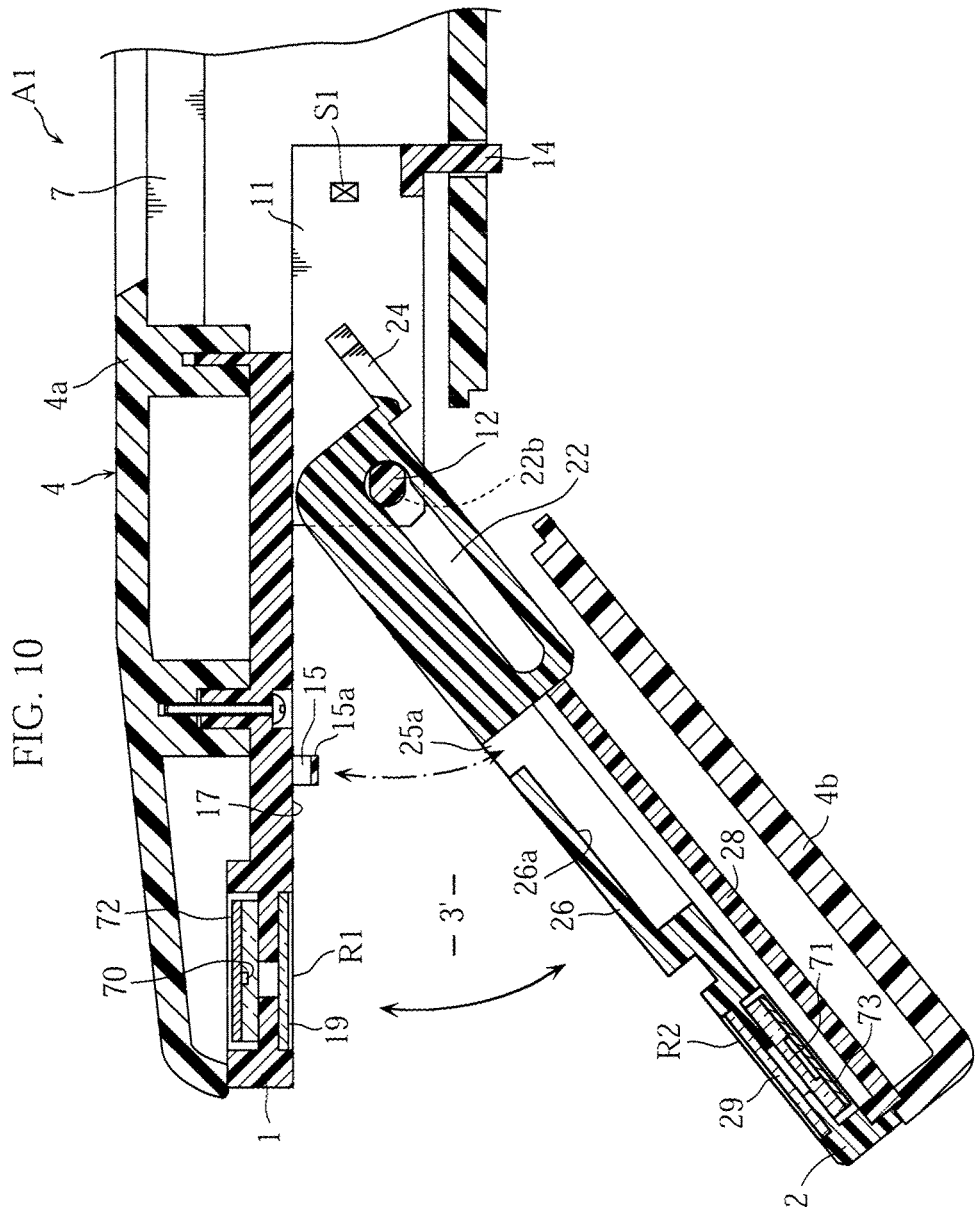
FIG. 10 is a sectional view, taken on line X-X of FIG. 3, of a relevant portion.

In cleaning the light transmissive members 19 and 29, the first and second members 1 and 2 are displaced as shown in FIGS. 2 and 9 and then set in the second state shown in FIGS. 3 and 10. In establishing such setting, first, the projection 14 is pressed upwardly as indicated by arrow N1 in FIG. 8 to a position at which the large width portion 14a of the projection 14 fails to engage the frame 24. By so doing, the locked condition of the first and second members 1 and 2 is released and then the second member 2 is moved forwardly of the first member 1 to establish the state shown in FIGS. 2 and 9. In this state, each of the projecting portions 12 is positioned in the large width portion 22b of the associated guide slot 22 and, hence, the second member 2 can be rotated downwardly to establish the second state shown in FIGS. 3 and 10. At the time of the rotation, the projections 15 come off the large width portions 25a of the slits 25. Accordingly, the projections 15 do not hinder the rotation.

When the first and second members 1 and 2 are set in the second state, the light transmissive members 19 and 29 front on the space 3' and hence is exposed to outside of the portable analyzer A1. For this reason, the light transmissive members 19 and 29 can be cleaned easily and appropriately. The cleaning can be achieved by rubbing the surfaces of the light transmissive members 19 and 29 with a rolling pin for example.

In the cleaning, there is no need to perform a troublesome and complicated operation such as to disassemble the portable analyzer A1 into plural parts. Accordingly, it is possible to eliminate the possibility that some parts are lost due to the disassembly of the portable analyzer A1. Switching from the first state to the second state is achieved by moving the second member 2 forwardly of the first member 1 by a predetermined distance and then rotating the second member 2 downwardly. This operation does not need any tool such as a screwdriver. Therefore, such switching can be achieved easily and quickly with reduced operational burden on the user.

After completion of the cleaning, the portable analyzer A1 is returned into the first state. In this returning operating, the second member 2 is rotated toward the first member 1 and then moved backward in reverse of the above-describe series of steps. Therefore, the returning operation is also easy. In the case where the second member 2 is not returned into its proper original position because of its insufficient backward movement, the data processing section 5 detects that fact by means of the sensor S1 and causes the display device 7 to provide a notification to that effect. Therefore, it is possible to avoid an inconvenience that the portable analyzer A1 is left or used without being properly returned into the original first state.

Since the guide surface 26a is inclined downwardly in the forward direction, the vertical play of the sandwiched portion 26 between the horizontal portions 15a and the downwardly oriented surface 17 of the first member 1 decreases gradually as the second member 2 moves backward from the state shown in FIGS. 2 and 9. Therefore, the operation to set the sandwiched portion 26 in the play-free condition shown in FIG. 7 can be performed smoothly. When the second member 2 is forwardly moved from the first state even slightly, the aforementioned play takes place to reduce the frictional resistance, thereby making it possible to slide the second member 2 smoothly with a weak force. This ensures good operability.

FIGS. 11 to 16C illustrate other embodiments of the present invention. In these figures, parts which are identical with or similar to the corresponding parts of the foregoing embodiment are denoted by like symbols.

Figure 11:
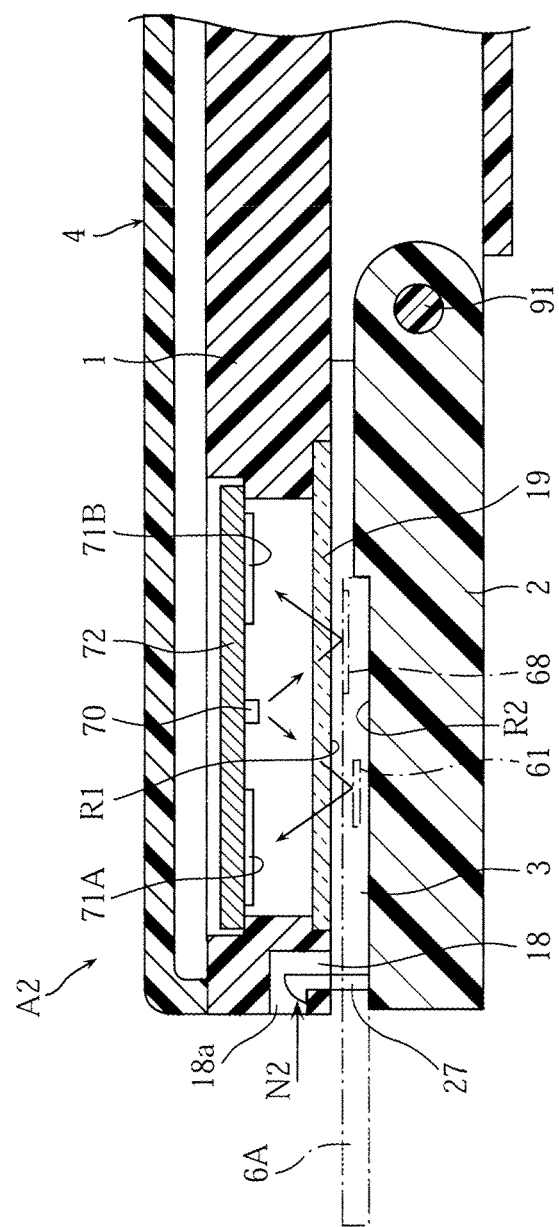
FIG. 11 is a sectional view of a relevant portion for illustrating another exemplary portable analyzer according to the present invention.

A portable analyzer A2 illustrated in FIG. 11 employs a reflection type specimen analyzing system. The second member 2 be rotated as shown in FIG. 12 without the need for sliding operation.

More specifically, a sampling implement 6A for use with the portable analyzer A2 has a light reflecting portion 68 of high reflectance in addition to the reaction portion 61 for allowing a specimen and a reagent to react with each other. Light emitted from the light source 70 is applied to the reaction portion 61 and the light reflecting portion 68, while reflected light from the reaction portion 61 and that from the light reflecting portion 68 are received by two light-receiving devices 71A and 71B, respectively. Signals corresponding to the lights received are outputted to the data processing section 5 (not shown in FIG. 11). The data processing section 5 determines a glucose level based on the output signal from the light-receiving device 71A while determining the transmittance of the light transmissive member 19 based on the output signal from the light-receiving device 71B. Specifically, when the output signal from the light-receiving device 71B is lower than a predetermined level, the data processing section 5 determines that the light transmissive member 19 is stained and provides a notification to that effect by utilizing the display device 7. The two light-receiving devices 71A and 71B are mounted on the substrate 72 mounted with the light source 70, the substrate 72 being mounted on the first member 1. The light transmissive member 19 is located in the first region R1. For this reason, the second region R2 is not provided with any optical component. The second region R2 may have any structure that can simply serve the purpose of forming the hole 3 when positioned close to the first region R1 in opposed relation while supporting the sampling implement 6A inserted into the hole 3.

The second member 2 has a rear end portion coupled to the first member 1 or the case 4 by means of a shaft 91 and is vertically rotatable about the shaft 91. The first and second members 1 and 2 are provided at their front end portions with a hole 18 and a projection 27 for engagement with each other. In the first state shown in FIG. 11, the upper end portion of the projection 27 is inserted into the hole 18 and engages a sidewall portion of the hole 18 to lock the second member 2 so that the second member 2 is inhibited from rotating downwardly. The hole 18 has an open portion 18a on its front side. When the projection 27 is pressed backwardly from the open portion 7a as indicated by arrow N2 in FIG. 11, the engagement between the projection 27 and the sidewall portion of the hole 18 is released to allow the second member 2 to rotate downwardly.

Figure 12:
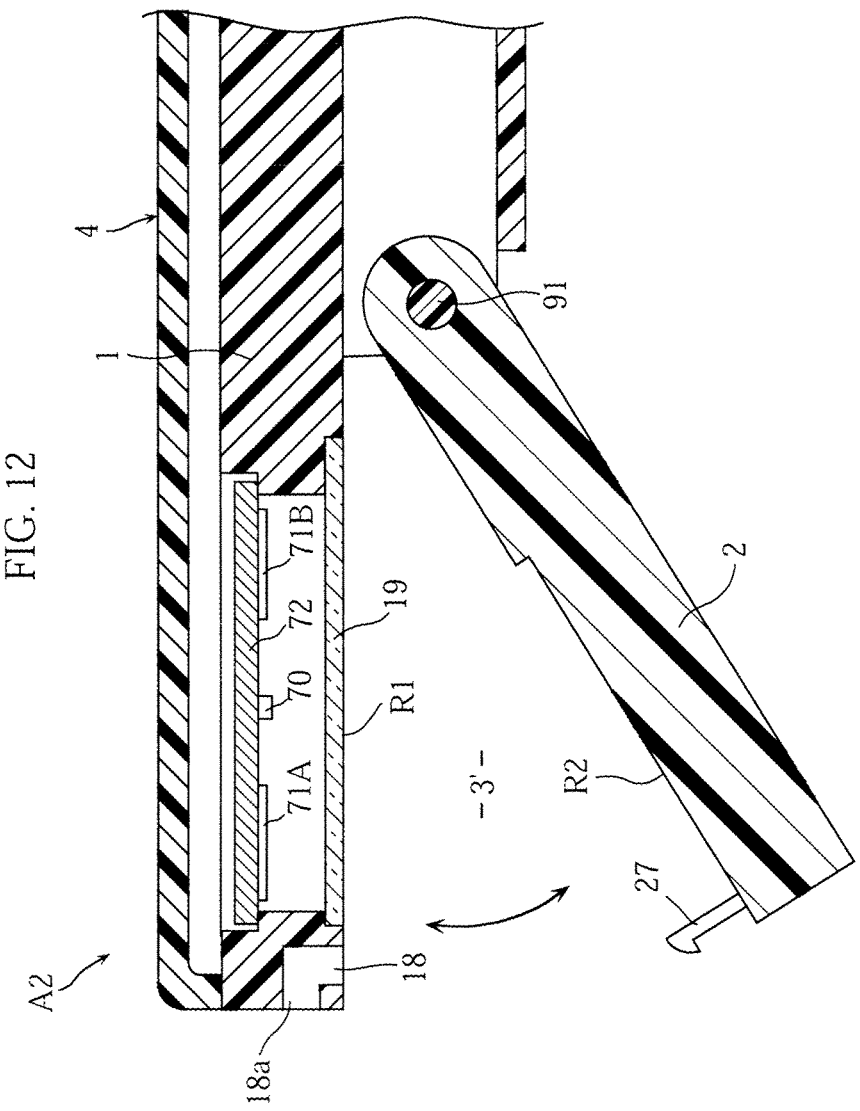
FIG. 12 is a sectional view of a relevant portion for illustrating an operating state of the portable analyzer illustrated in FIG. 11.

According to the present embodiment, when the second member 2 is rotated from the first state shown in FIG. 11 to establish the second state shown in FIG. 12, the light transmissive member 19 becomes exposed. Therefore, the light transmissive member 19, when stained, can be cleaned easily and appropriately. Unlike the foregoing embodiment, the present embodiment does not need to slide the second member 2 forwardly and, hence, the required operation is simplified and facilitated by the elimination of the sliding operation. In the first state shown in FIG. 11, the first and second members 1 and 2 can be maintained in a predetermined positional relation by engagement between the projection 27 and the sidewall of the hole 18. With only the engagement means using the projection 27 and the hole 18, the precision with which the first and second members 1 and 2 are positioned relative to each other is sometimes slightly inferior to that in the foregoing embodiment. However, unlike the portable analyzer A1 according to the foregoing embodiment, the portable analyzer A2 according to the present embodiment employs the reflection type analyzing system in which the light source 70 and the light-receiving devices 71A and 71B are collectively located on the first member 1 side. For this reason, even when some error occurs in the positional relation between the first and second members 1 and 2, any error does not take place in the positional relation between the light source 70 and the light-receiving devices 71A and 71B and, therefore, there is no possibility of a problem that the specimen analyzing accuracy lowers significantly. As can be appreciated from the present embodiment, the present invention may employ a simple arrangement in which the first and second members 1 and 2 are coupled to each other for relative rotation without sliding.

Figure 13:
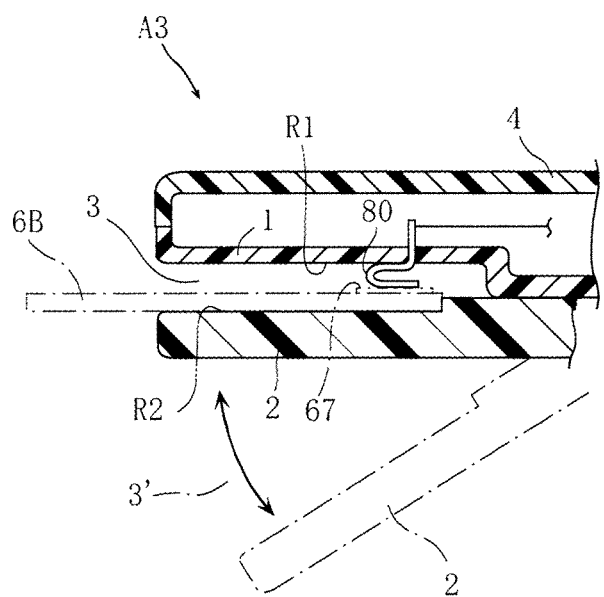
FIG. 13 is a sectional view of a relevant portion for illustrating another exemplary portable analyzer according to the present invention.

A portable analyzer A3 illustrated in FIG. 13 is of a type which analyzes a specimen by an electrical or electrochemical technique. The first region R1 is provided with an electrode 80 to be brought into contact with an electrode 67 of a sampling implement 6B for application of voltage. The portable analyzer A3 is designed to apply voltage to a reaction portion in which the specimen and a reagent react with each other, pick up a current responding thereto and analyze the specimen based on the electrical characteristics of the reaction portion. Since this system is similar to that of the analyzer described in Patent Document 2, detailed description of the arrangement of the portable analyzer A3 is omitted. When the electrode 80 is stained in the portable analyzer A3, it is possible the electrical conductivity thereof is lowered. In the first state in which first and second members 1 and 2 are positioned close to each other in opposed relation, the electrode 80 is located within the hole 3 and hence is difficult to clean. However, when the second state is established by rotating the second member 2 as depicted by a phantom line of FIG. 13 according to the present invention, the electrode 80 becomes exposed to outside and hence can be easily cleaned.

Figure 14A:
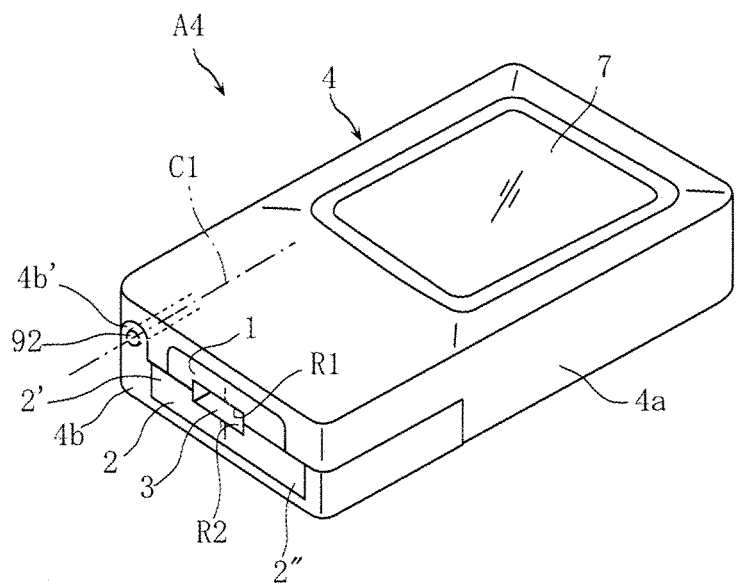
FIGS. 14A and 14B are perspective views of a relevant portion for illustrating another exemplary portable analyzer according to the present invention.
Figure 14B:
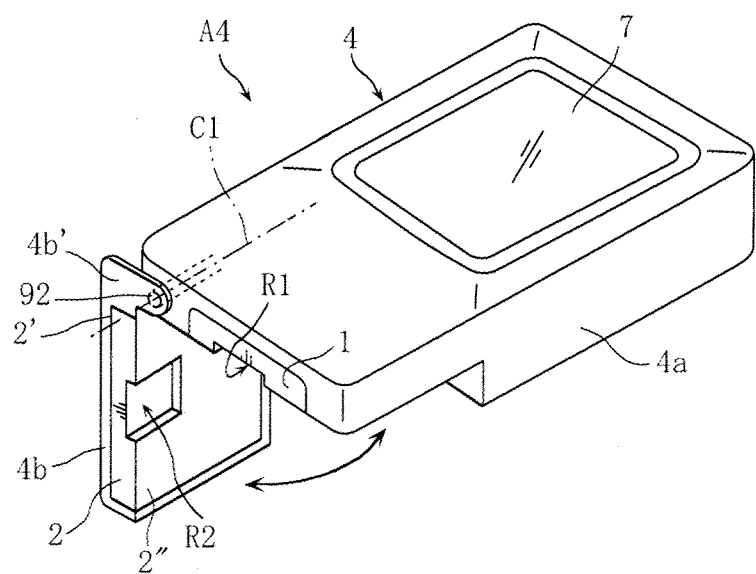

In a portable analyzer A4 illustrated in FIGS. 14A and 14B, one side edge portion 2' of the second member 2 or one side edge portion 4b' of the auxiliary portion 4b of the case 4 is connected directly or indirectly to the first member 1 by means of a shaft 92. The first and second members 1 and 2 are rotatable relative to each other about a central axis C1 of the shaft 92 extending in the front-back direction of the case 4. With this arrangement, the first and second members 1 and 2 can be switchably set in the first state in which the first and second members 1 and 2 are positioned close to each other in opposed relation to form the hole 3 as shown in FIG. 14A and in the second state in which the other side edge portion 2" of the second member 2 is largely opened downwardly of the first member 1 as shown in FIG. 14B. In FIGS. 14A and 14B, the first and second regions R1 and R2 and their peripheral structures are shown in a simplified fashion. This holds true for FIGS. 15A to 16C.

In the present embodiment also, the first and second regions R1 and R2 are properly exposed to outside when the second state shown in FIG. 14B is established. Therefore, these regions can be cleaned easily and appropriately. As can be appreciated from the present embodiment, in rotating the first and second members 1 and 2 relative to each other, the first and second members 1 and 2 need not necessarily rotate so as to open the front end portions thereof, but may rotate so as to open their portions other than the front end portions.

Figure 15A:
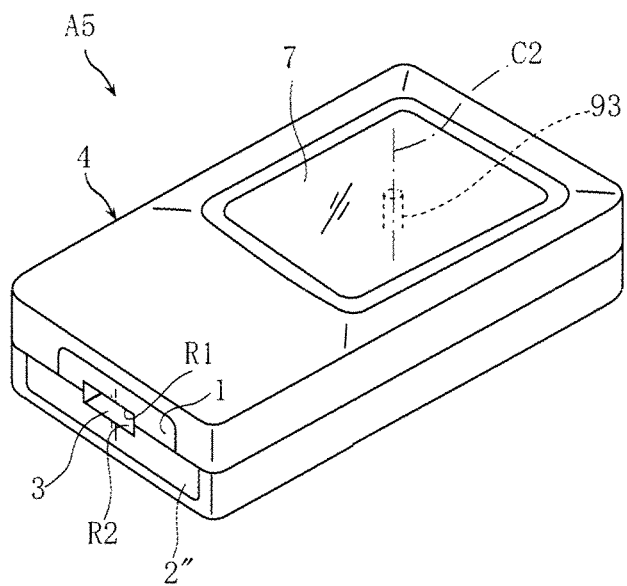
FIGS. 15A and 15B are perspective views of a relevant portion for illustrating another exemplary portable analyzer according to the present invention.
Figure 15B:
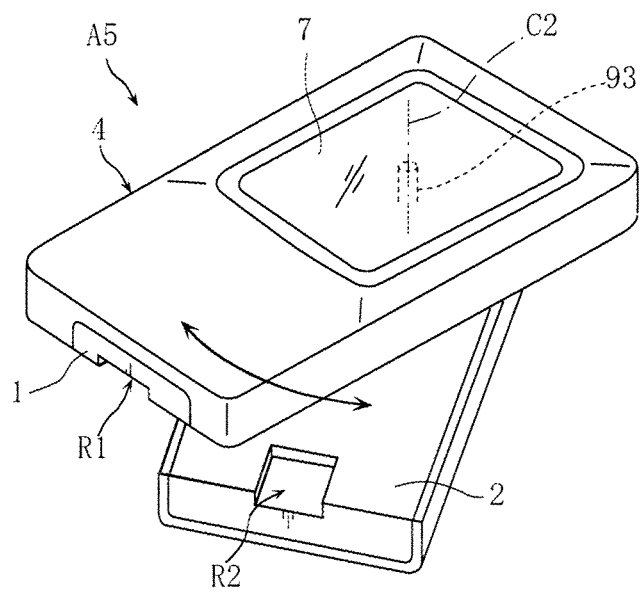

In a portable analyzer A5 illustrated in FIGS. 15A and 15B, the first and second members 1 and 2 are directly or indirectly coupled to each other for relative rotation by means of a shaft 93. The first and second members 1 and 2 are horizontally rotatable relative to each other about a central axis C2 of the shaft 93 extending vertically. With this arrangement, the first and second members 1 and 2 can be switchably set in the first state in which the first and second members 1 and 2 are positioned close to each other in opposed relation to form the hole 3 as shown in FIG. 15A and in the second state in which the first and second regions R1 and R2 are both exposed to outside by failure to face each other as shown in FIG. 15B. In the present embodiment also, the first and second regions R1 and R2 can be cleaned easily and appropriately.

Figure 16A:
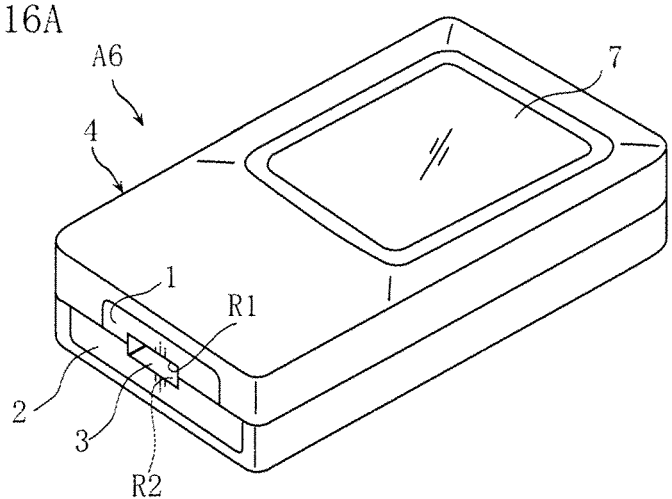
FIGS. 16A to 16C are perspective views of a relevant portion for illustrating another exemplary portable analyzer according to the present invention.
Figure 16B:
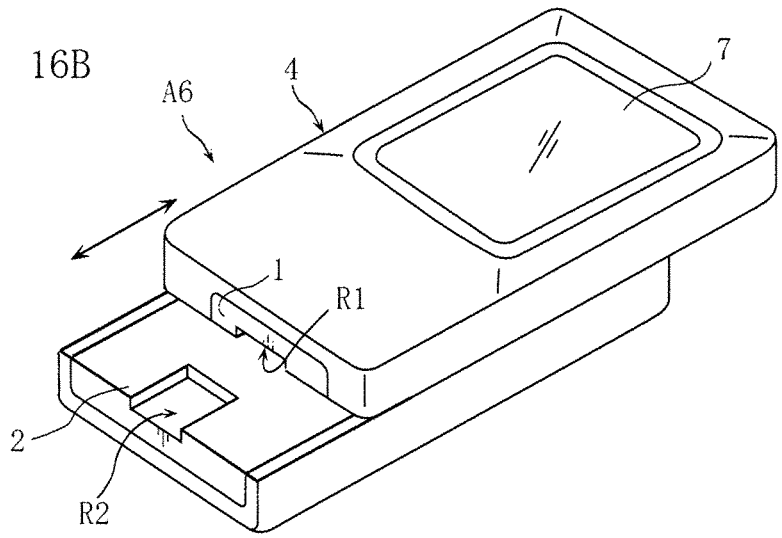
Figure 16C:
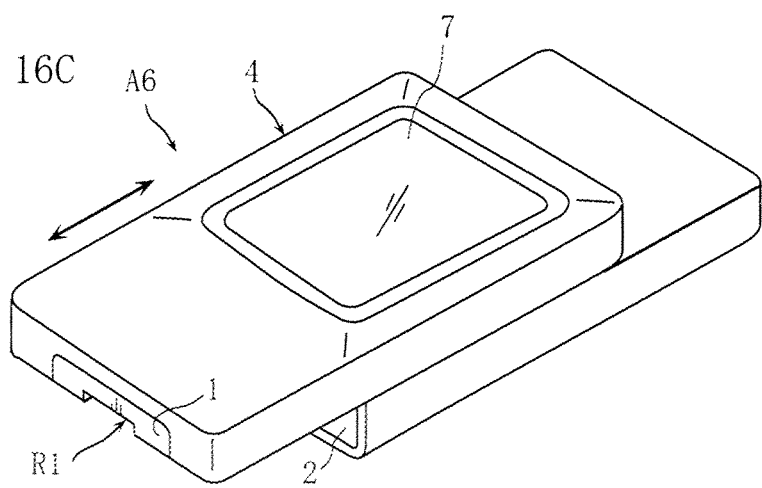

In a portably analyzer A6 illustrated in FIGS. 16A to 16C, the first and second members 1 and 2 are slidable relative to each other in their front-back direction. Besides the state in which the first and second regions R1 and R2 are opposed to each other to form the hole 3 as shown in FIG. 16A, the first and second members 1 and 2, which are designed to be slidable, can be set in at least one of the states shown in FIGS. 16B and 16C. In the state shown in FIG. 16B, the second region R2 is protruded forwardly of the first member 1 and is exposed to outside. In the state shown in FIG. 16C, the first region R1 is protruded forwardly of the second member 2 and is exposed to outside. Examples of usable means for making the first and second members 1 and 2 slidable relative to each other include means having a guide slot formed at one of the first and second members 1 and 2 and extending in the front-back direction thereof and a projecting portion formed at the other which can be engaged in the guide slot and move longitudinally thereof.

In the present embodiment, either or both of the first and second regions R1 and R2 can be exposed to outside as shown in FIGS. 16B and 16C, though the first and second members 1 and 2 fail to rotate relative to each other. Therefore, either or both of the first and second regions R1 and R2 can be cleaned easily and appropriately. As can be appreciated from the present embodiment, the present invention may employ an arrangement in which at least one of the first and second regions can be exposed to outside by simply sliding the first and second members relative to each other without rotating the first and second members relative to each other.

The present invention is not limited to the embodiments described above. The specific structures and features of different parts of the portable analyzers according to the present invention may be variously changed in design.

The first and second members according to the present invention may have any structure that can form a hole for insertion of a sampling implement therein when the first and second members are positioned close to each other in opposed relation and are not limited to the specific shapes and sizes thereof. Each of the first and second members need not necessarily be a single member, but may comprise plural members in combination. Though the coupling between the first and second members is essential, the coupling need not necessarily be direct coupling, but may be indirect coupling via the case or other member.

The hole for insertion of the sampling implement therein may have any shape that allows the sampling implement to be inserted therein at least partially. It is possible employ an arrangement in which the front open end of the hole is normally covered with an appropriate cover to block intrusion of dust and the like into the hole and uncovered only during the analyzing operation. The sampling implement may be selected from various sampling implements regardless of whether or not a reagent is provided therein.

The analyzing means according to the present invention simply has the function of analyzing a specimen. There is no limitation on the type of the specimen to be analyzed or on the specific elements thereof. For example, an element in blood other than glucose or a specific element in urine may be subjected to measurement. The term "portable" of the portable analyzer according to the present invention is meant to indicate an analyzer having a size and shape suitable for portable use by being gripped by one hand for example, unlike a relatively large-sized analyzer of the so-called installation or stationary type.

The invention claimed is:

1. A portable analyzer comprising:
   an opening configured for insertion of sampling implement therein; and
   a means for analysis programmed to analyze a specimen present on the sampling implement when the sampling implement is inserted into the opening,
   wherein the opening is formed by having a first member and a second member in an opposed relationship to each other and positioned close to or in contact with each other,
   wherein the first member includes a first region corresponding to a portion of the internal surface of the opening, and the second member includes a second region corresponding to a different portion of the internal surface of the opening,
   wherein the first and the second members are coupled to each other by a coupling portion that is configured to allow the first and the second members to move relative to each other, the relative movement enabling selective switching from a first state in which the first and the second regions are positioned sufficiently close to each other to allow insertion of the sampling implement, to a second state in which the first and the second regions are spaced sufficiently apart such that at least one of the first and the second regions is exposed to the exterior of the analyzer,
   wherein the coupling portion is further configured so as to provide a central axis about which the first member and the second member can rotate relative to each other,
   wherein the first and the second members set in the first state are configured to rotate relative to each other by a predetermined amount of displacement in fixed directions by a means for sliding when transitioning to the second state.

2. The portable analyzer according to claim 1, wherein:
   the means for sliding includes a guide slot provided on one of the first and the second members and having a small width portion extending in the fixed directions and a large width portion extending continuously with one end of the small width portion, and a projecting portion provided at the other for engagement in the guide slot and having a noncircular sectional shape;
   when the projecting portion is engaged in the small width portion, the first and the second members are allowed to slide relative to each other in the fixed directions with their relative rotation being inhibited; and
   when the projecting portion is engaged in the large width portion as a result of the relative sliding of the first and the second members, the first and second members are allowed to rotate relative to each other.

3. The portable analyzer according to claim 1, further comprising an auxiliary guide configured to guide the second member in a direction to bring the second member closer to the first member in returning the first and the second members from a displaced state to the first state and to keep the relative position between the first and the second members after a return to the first state.

4. The portable analyzer according to claim 3, wherein
   the auxiliary guide has an engagement projection provided on one of the first and second members and a guide surface provided on the other,
   the projection being configured to engage the guide surface so as to inhibit the first and the second members in the first state from separating from each other in opposite directions.

5. The portable analyzer according to claim 4, wherein the guide surface is inclined at least partially to provide a play between the first and the second members in the first state when the second member moves forward of the first member.

6. The portable analyzer according to claim 1, further comprising a case configured to accomodate the means for analysis therein while covering a periphery of the first and the second members in the first state,
   the case being divided into plural portions which cover the first and the second members individually and which move relative to each other as the first and the second members move relative to each other.

7. The portable analyzer according to claim 1, further comprising a means for detecting the relative positioning of the first and the second members to determine whether or not the first and second members are correctly set in the first state, wherein
   in response to a determination that the first and the second members are not correctly set in the first state, an alarm operation is configured to provide notification to that effect.

8. The portable analyzer according to claim 1, further comprising a locking mechanism configured to inhibit relative movement of the first and the second members to maintain the first and the second members in the first state while allowing relative movement of the first and second members in response to a predetermined operation.

9. The portable analyzer according to claim 1, wherein:
   the means for analysis is programmed to carry out measurement on a predetermined element of the specimen by applying light to the specimen under a predetermined condition and receiving transmitted light or reflected light from the specimen;
   at least one of the first and the second members is provided with a light transmissive member which allows light to pass therethrough; and
   the light transmissive member is configured to become exposed to outside the exterior of the analyzer to allow cleaning thereof when the first and the second members are set in the second state.

10. The portable analyzer according to claim 9, wherein:
the means for analysis is programmed to detect whether or not stain is present on the light transmissive member based on the amount of transmitted light through the light transmissive member; and in response to detection of stain on the light transmissive member, an alarm operation is configured to provide notification to that effect.

11. The portable analyzer according to claim 1, wherein:
the means for analysis is provided with an electrode to be placed in at least one of the first and the second regions so as to come into contact with a predetermined portion of the sampling implement and is further programmed to carry out measurement of a predetermined element of the specimen based on information provided by the electrode; and the electrode becomes exposed to the exterior of the analyzer to allow cleaning thereof when the first and the second members are set in the second state.

12. The portable analyzer according to claim 1, wherein the means for analysis is programmed to measure a blood glucose level when the specimen is blood.

* * * * *